United States Patent [19]

Mulders et al.

[11] 4,107,411
[45] Aug. 15, 1978

[54] METHOD OF PREPARING SALTS OF POLY-ALPHA-HYDROXYACRYLIC ACID

[75] Inventors: Julien Mulders, Dworp; Jacques Gilain, Brussels, both of Belgium

[73] Assignee: Solvay & Cie., Brussels, Belgium

[21] Appl. No.: 622,503

[22] Filed: Oct. 15, 1975

Related U.S. Application Data

[63] Continuation of Ser. No. 489,718, Jul. 18, 1974, abandoned.

[30] Foreign Application Priority Data

Jul. 18, 1973 [LU] Luxembourg .................... 68037

[51] Int. Cl.$^2$ .................... C08F 2/10; C08F 120/06
[52] U.S. Cl. .................... 526/75; 260/539 R; 526/229; 526/230; 526/232; 526/292
[58] Field of Search ............... 526/75, 292, 229, 230, 526/232; 260/539 R

[56] References Cited

U.S. PATENT DOCUMENTS

| | | | |
|---|---|---|---|
| 2,286,264 | 6/1942 | Croom et al. .................... | 526/292 |
| 2,499,811 | 3/1950 | Barnes et al. .................... | 526/292 |
| 2,501,647 | 4/1950 | Ney, Jr. .................... | 526/292 |
| 2,514,305 | 7/1950 | Barnes .................... | 526/292 |
| 2,515,686 | 7/1950 | Barnes et al. .................... | 526/292 |
| 2,576,821 | 11/1951 | Barnes .................... | 526/292 |
| 2,647,922 | 8/1953 | Ney, Jr. .................... | 526/75 |
| 2,736,744 | 2/1956 | Croom et al. .................... | 526/292 |
| 2,870,193 | 1/1959 | Pollack .................... | 526/292 |
| 2,964,488 | 12/1960 | Anspon et al. .................... | 526/292 |
| 2,966,471 | 12/1960 | Anspon .................... | 526/292 |
| 3,845,095 | 10/1974 | Bechstein et al. .................... | 260/539 R |
| 3,857,882 | 12/1974 | Auer et al. .................... | 260/539 R |
| 3,890,288 | 6/1975 | Vogt et al. .................... | 526/292 |
| 3,890,291 | 6/1975 | Vogt et al. .................... | 526/292 |
| 3,984,439 | 10/1976 | Vanlautem et al. .................... | 526/232 |

*Primary Examiner*—Alan Holler
*Attorney, Agent, or Firm*—Spencer & Kaye

[57] ABSTRACT

Salts of poly-α-hydroxyacrylic acid or their alkyl derivatives are obtained by thermally dehydrochlorinating α, β-dichloro-propionic acid or its alkyl derivatives into the corresponding α-chloroacrylic acid, polymerizing the α-chloroacrylic acid in water to obtain a solid product and neutralizing the solid product with an aqueous solution of alkali metal hydroxide or ammonium hydroxide.

The poly-α-hydroxyacrylates are useful as sequestering agents or builders.

24 Claims, No Drawings

METHOD OF PREPARING SALTS OF POLY-ALPHA-HYDROXYACRYLIC ACID

CROSS-REFERENCE TO RELATED APPLICATION

This application is a continuation of application Ser. No. 489,718, filed July 18, 1974, now abandoned.

BACKGROUND OF THE INVENTION

The present invention relates to a process for the preparation of water-soluble salts of poly-α-hydroxyacrylic acid or its alkyl derivatives.

Various methods have already been proposed for synthesizing these polyelectrolytes which can be used as agents for sequestering metal ions and as builders in detergents as described in Belgian Patent No. 776,705 of Dec. 15, 1971 in the name of Solvay and Cie.

C. S. Marvell et al (J. Am. Chem. Soc., 1940, 62, pp. 3495–3498) have proposed a method of synthesis starting from methyl acrylate, which is a very expensive starting material. In Belgian Patent No. 786,464 of July 19, 1972, there is described a more economical process for preparing salts of poly-α-hydroxyacrylic acid, starting from acrylic acid. Although this process is more economical, it nevertheless requires several intermediate steps and the consumption of reagents is rather high.

German Patent Application DOS No. 2,061,584 of Dec. 15, 1970 in the name of HENKEL u. Co. aims to provide a process for synthesizing these polyelectrolytes by treating an α,β-dihalogeno-propionic acid with an alkali and converting the product obtained into a water-soluble salt. This process also possesses the disadvantage of requiring rather large amounts of reagents, and especially of sodium hydroxide.

SUMMARY OF THE INVENTION

The aim of the present invention is a method for synthesizing water-soluble salts of poly-α-hydroxyacrylic acid or its alkyl derivatives, which requires only a small amount of reagents, and particularly of sodium hydroxide.

The present invention, as embodied and as broadly described, provides a process for the preparation of water-soluble salts of poly-α-hydroxyacrylic acid or its alkyl derivatives comprising converting α,β-dichloropropionic acid, or its alkyl derivatives, into the corresponding α-chloro-acrylic acid by thermal dehydrochlorination in the gas phase in the presence of a catalyst, polymerizing the resulting α-chloro-acrylic acid in water in the presence of a free radical polymerization catalyst to obtain a solid product, and neutralizing the solid product with an aqueous solution of an alkali metal hydroxide or ammonium hydroxide. The salt of the corresponding poly-α-hydroxyacrylic acid is thereby obtained.

Generally, the alkyl derivatives of α,β-dichloropropionic acid contain in their β-position one or two lower alkyl groups with 1 to 3 carbon atoms in each group.

DETAILED DESCRIPTION OF THE INVENTION

The process of the present invention can be for example successfully applied to the preparation of sodium, potassium or ammonium salts of poly-α-hydroxyacrylic acid or of polyα-hydroxy-β-methacrylic acid.

The starting α,β-dichloro-propionic acid and its alkyl derivatives generally correspond to the formula

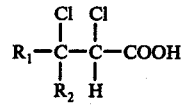

wherein $R_1$ and $R_2$ independently represent a hydrogen atom or an alkyl group containing 1 to 3 carbon atoms. Thus, $R_1$ and $R_2$ can be the same or different. The α,β-dichloro-propionic acid can be introduced into the reactor wherein the conversion to the α-chloro-acrylic acid takes place, either in the pure state or diluted with an inert compound or with a solvent. In the latter case, a solvent which is inert under the reaction conditions, for example a chlorinated hydrocarbon such as perchloroethylene, carbon tetrachloride and the like, or water, can be chosen.

The dehydrochlorination of the α,β-dichloro-propionic acid is carried out in the gas phase in the presence of a suitable catalyst such as one or more copper, lead, calcium, zinc, cadmium, iron, cobalt, bismuth, titanium, manganese, barium or aluminum halides and/or oxides or other similar substances possessing a surface effect, such as silica gel, activated charcoal, activated aluminum oxide and the like. Calcined aluminum oxide (corundum) or aluminum fluoride will preferably be used. The catalyst can be used in a fixed bed or a fluidized bed.

The pyrolysis temperature during dehydrochlorination is preferably between 200° and 400° C. At temperatures below 200° C, the degree of conversion of α,β-dichloro-propionic acid to α-chloro-acrylic acid decreases, while at temperatures above 400° C, it is found that acrylic acid appears in addition to α-chloro-acrylic acid. The pressure during dehydrochlorination preferably is maintained at between 0.8 and 10 kg/cm², but lower or higher pressures can also be used.

The dehydrochlorination product issues from the reactor as a gaseous mixture of hydrogen chloride and α-chloro-acrylic acid. This mixture is then separated by, for example, condensing the α-chloro-acrylic acid. The α-chloro-acrylic acid is then polymerized in water in the presence of a polymerization catalyst at a temperature of between 40° and 100° C, and preferably between 60° and 80° C to bring about hydrolysis and polymerization.

The concentration of the α-chloro-acrylic acid in the aqueous solution can vary between wide limits. Concentrations of from 0.1 to 4 and advantageously from 0.7 to 3 moles per liter are preferred. Lower concentrations can also be used, but they render the process less interesting from an economical point of view because the productivity of the reactors is low. Higher concentrations are more difficult to use because the reaction mixture sets solid during the polymerization.

Any of the polymerization catalysts with a radical action can be used, for example, organic peroxides such as benzoyl peroxide, dibenzoyl peroxide, cumyl hydroperoxide and the like, inorganic per-compounds such as hydrogen peroxide, sodium perborate, potassium persulphate and the like, redox initiators and diazo compounds. Reference can, for example, be made to the work by D. A. Smith, *Addition Polymers, Formation and Characterization*, Butterworth, London, 1968, p. 22–25.

The amount of catalyst used in this polymerization step depends on the amount of α-chloro-acrylic acid present in the aqueous solution. The molar ratio of catalyst to α-chloroacrylic acid is generally between about 0.0001 to 0.1 moles of catalyst per mole of α-chloro-acrylic-acid.

For example, potassium persulphate will be used as the polymerization catalyst, in a $K_2S_2O_8$/α-chloro-acrylic acid molar ratio of between 0.001 and 0.1 moles of $K_2S_2O_8$ per mole of α-chloro-acrylic acid, and preferably between 0.005 and 0.05 moles of $K_2S_2O_8$ per mole of α-chloro-acrylic acid.

The product obtained in the polymerization step is insoluble in water and is separated from the reaction mixture by filtration, spinning and drying. Other known methods of separation can also be used.

This solid product is then introduced into an aqueous solution of an alkali metal hydroxide or ammonium hydroxide to prepare the corresponding salt of poly-α-hydroxyacrylic acid. The amount of hydroxide used is the stoichiometrical amount.

The aqueous solution of the hydroxide is generally very concentrated and contains more than 0.1 and preferably more than 1 mole of hydroxide per liter of solution.

Saturated solutions are advantageously used. When the hydroxide is solid, it is also possible to use saturated solutions containing excess amounts of solid metal alkali hydroxide.

The salt of poly-α-hydroxyacrylic acid obtained in the neutralization step is soluble in water. It can be separated from its solution in water by evaporation of the water or by precipitation with methanol and generally corresponds to the formula

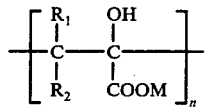

where $R_1$ and $R_2$ independently represent hydrogen or an alkyl group containing 1 to 3 carbon atoms, M is selected from the group consisting of alkali metal and ammonium and $n$ represents an integer at least equal to 3. Most frequently the degree of polymerization represented by $n$ is from about 50 to about 10,000 and most preferably from about 100 to about 8000.

The following examples illustrate the present invention. They do not, however, imply any limitation.

EXAMPLE 1

(a) Conversion of α,β-dichloro-propionic acid to α-chloro-acrylic acid

The reactor used consists of a stainless steel tube with a diameter of 2.54 cm and a length of 120 cm, heated externally.

The catalyst was prepared by calcination of Ketjen alumina for 10 hours at 1,200° C. It is then in the form of cylinders of diameters of 3 mm and length 4 mm. 500 ml of this catalyst are placed in the reactor.

α,β-dichloro-propionic acid is introduced at the rate of 1.36 mols/hour into the reactor, which is packed with catalyst and heated to a temperature of about 300° C, together with nitrogen for dilution purposes, which is introduced at the rate of 4.02 mols/hour. The dehydrochlorinated product issuing from the reactor consists of 100% of α-chloro-acrylic acid, and hydrogen chloride produced during the reaction issues at the rate of 1.39 mols/hour. The mixture of α-chloro-acrylic acid and hydrogen chloride is separated by simply condensing the α-chloro-acrylic acid.

The dehydrochlorination pressure is about 1 kg/cm².

(b) Treatment of α-chloro-acrylic acid with water 20 g (0.188 mol) of α-chloro-acrylic acid free from hydrogen chloride, obtained in a), are dissolved in 200 g of water. 0.0094 mol of potassium persulphate is introduced into the reaction mixture and the temperature is raised to 60° C for 2 hours. 10.9 g of solid product are collected.

This product is then introduced into a solution of sodium hydroxide. The sodium poly-α-hydroxyacrylate produced is then precipitated by means of methanol. 17.1 g of final product are collected.

EXAMPLE 2

(a) Conversion of α,β-dichloro-propionic acid to α-chloro-acrylic acid

α,β-dichloro-propionic acid is introduced, at the rate of 0.8 mol/hour, into the same reactor as in Example 1, together with perchloroethylene introduced at the rate of 0.5 mol/hour and nitrogen introduced at the rate of 4.02 mols/hour. A dehydrochlorination product comprising 100% of α-chloro-acrylic acid is collected in the same way as in Example 1.

The dehydrochlorination temperature in the reactor is about 300° C and the pressure is about 1 kg/cm².

(b) Treatment of α-chloro-acrylic acid with water

The procedure of Example 1 is followed.

It will be understood that the above description of the present invention is susceptible to various modifications, changes and adaptations, and the same are intended to be comprehended within the meaning and range of equivalents of the appended claims.

What is claimed is:

1. A process for preparing water-soluble salts of poly-α-hydroxyacrylic acid or its alkyl derivatives, comprising:
   (a) thermally dehydrochlorinating, in the gas phase in the presence of a catalyst, α,β-dichloro-propionic acid, or its alkyl derivatives, to the corresponding α-chloro-acrylic acid;
   (b) polymerizing the resulting α-chloro-acrylic acid in water in the presence of a free radical polymerization catalyst to obtain a solid product; and
   (c) neutralizing the solid product with an aqueous solution of an alkali metal hydroxide or ammonium hydroxide.

2. The process according to claim 1, wherein the thermal dehydrochlorination of α,β-dichloro-propionic acid to α-chloro-acrylic acid is carried out in the presence of calcined alumina as the catalyst and at a temperature of between 200° and 400° C.

3. The process according to claim 1, wherein the α,β-dichloro-propionic acid is diluted with an inert solvent.

4. The process according to claim 3, wherein the solvent is a chlorinated hydrocarbon or water.

5. The process according to claim 1 wherein the polymerization of the α-chloro-acrylic acid in water is carried out in the presence of potassium persulphate as the polymerization catalyst.

6. The process according to claim 5 wherin the potassium persulphate/α-chloro-acrylic acid molar ratio is between 0.001 and 0.1 moles of potassium persulphate per mole of α-chloro-acrylic acid.

7. The process according to claim 6 wherein the molar ratio is between 0.005 and 0.05 moles of potassium persulphate per mole of α-chloro-acrylic acid.

8. The process according to claim 1 wherein the polymerization of the α-chloro-acrylic acid in water is carried out at a temperature of between 40° and 100° C.

9. The process according to claim 8 wherein the polymerization of the α-chloro-acrylic acid in water is carried out at a temperature of between 60° and 80° C.

10. The process according to claim 1 wherein the starting α,β-dichloro-propionic acid and its alkyl derivatives correspond to the general formula

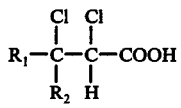

wherein R$_1$ and R$_2$ independently represent a hydrogen atom or an alkyl group containing 1 to 3 carbon atoms.

11. The process according to claim 1 wherein the α-chloro-acrylic acid obtained from the dehydrochlorination is condensed before it is polymerized.

12. A process for making a poly-α-hydroxyacrylic compound or its alkyl derivatives which comprises treating the corresponding α-chloroacrylic acid in an aqueous medium in the presence of a free radical polymerization catalyst to bring about polymerization and form a solid product.

13. The process according to claim 12 wherein α-chloroacrylic acid is treated.

14. The process according to claim 13 wherein the polymerization of the α-chloro-acrylic acid in the aqueous medium is carried out at a temperature of between 40° and 100° C.

15. A process according to claim 13 wherein the free radical polymerization catalyst is selected from the group consisting of organic peroxides, inorganic per-compounds, redox initiators and diazo compounds.

16. A process according to claim 15 wherein the organic peroxide is selected from the group consisting of benzoyl peroxide, dibenzoyl peroxide and cumyl hydroperoxide.

17. A process according to claim 15 wherein the inorganic per-compound is selected from the group consisting of hydrogen peroxide, sodium perborate and potassium persulphate.

18. A process according to claim 17 wherein the polymerization catalyst is potassium persulphate.

19. A process according to claim 18 wherein the potassium persulphate/α-chloroacrylic acid molar ratio is between 0.001 and 0.1 moles of potassium persulphate per mole of α-chloroacrylic acid.

20. A process according to claim 19 wherein the molar ratio is between 0.005 and 0.05 moles of potassium persulphate per mole of α-chloroacrylic acid.

21. In a process for making poly-α-oxyacrylic acid by contacting a solution of α-chloroacrylic acid with radical-yielding polymerization catalysts, heating and thereby hydrolyzing the resulting poly-α-chloroacrylic acid in aqueous solution with the resultant precipitation of solid poly-α-oxyacrylic acid, the improvement which comprises contacting and heating an aqueous α-chloroacrylic acid solution with the radical-yielding polymerization catalysts for a period of two hours while leaving the resulting poly-α-chloroacrylic acid unseparated, said heating being to temperatures within the range 40° and 100° C.

22. A process as claimed in claim 21, wherein potassium peroxo-disulfate-(VI) is used as the radical-yielding polymerization catalyst in proportions within the range 0.001 and 0.1 moles potassium peroxo-disulfate-(VI) per mole of α-chloroacrylic acid.

23. A process as claimed in claim 21, wherein the aqueous α-chloroacrylic acid solution having a radical-yielding polymerization catalyst or a redox system dissolved therein is maintained at temperatures within the range 40° and 80° C.

24. A process as claimed in claim 21, wherein an aqueous α-chloroacrylic acid solution containing the radical-yielding polymerization catalyst as claimed in claim 22 is heated to temperatures within the range 40° and 100° C.

* * * * *